(12) United States Patent
Alexandersson (10) Patent No.: US 11,986,635 B2
(45) Date of Patent: *May 21, 2024

(54) MEDICAMENT DELIVERY DEVICE

(71) Applicant: SHL MEDICAL AG, Zug (CH)

(72) Inventor: Oscar Alexandersson, Haninge (SE)

(73) Assignee: SHL Medical AG, Zug (CH)

( * ) Notice: Subject to any disclaimer, the term of this patent is extended or adjusted under 35 U.S.C. 154(b) by 247 days.

This patent is subject to a terminal disclaimer.

(21) Appl. No.: 17/590,973

(22) Filed: Feb. 2, 2022

(65) Prior Publication Data

US 2022/0152307 A1 May 19, 2022

Related U.S. Application Data

(63) Continuation of application No. 16/304,865, filed as application No. PCT/EP2017/060965 on May 9, 2017, now Pat. No. 11,273,259.

(30) Foreign Application Priority Data

Jun. 3, 2016 (SE) .................................. 1650778-2

(51) Int. Cl.
*A61M 5/24* (2006.01)
*A61M 5/20* (2006.01)
(Continued)

(52) U.S. Cl.
CPC .......... *A61M 5/24* (2013.01); *A61M 5/31501* (2013.01); *A61M 5/31535* (2013.01);
(Continued)

(58) Field of Classification Search
CPC .. A61M 5/24; A61M 5/31571; A61M 5/3204; A61M 5/3257; A61M 5/31501;
(Continued)

(56) References Cited

U.S. PATENT DOCUMENTS

2012/0203186 A1  8/2012  Vogt et al.

FOREIGN PATENT DOCUMENTS

| CN | 104394924 A | 3/2015 |
| CN | 105530969 A | 4/2016 |

(Continued)

OTHER PUBLICATIONS

International Search Report and Written Opinion for Int. App. No. PCT/EP2017/060965, dated Jul. 11, 2017.

(Continued)

*Primary Examiner* — Bradley J Osinski
(74) *Attorney, Agent, or Firm* — McDonnell Boehnen Hulbert & Berghoff LLP (57) ABSTRACT

A medicament delivery device is disclosed having a housing, an actuation mechanism capable of delivering doses of medicament from a medicament container and arranged with a delivery member, a shield, a guard movable within the housing, wherein the guard is operably connected to the actuation mechanism. A protective cap is releasably arranged on the housing and having a shield remover. A blocking element on the guard is movable between a blocking position and a release position and has an engagement surface to engage a proximal area of the housing. The blocking element engages with a surface of the shield remover to retain the blocking element in the blocking position. The engagement surface causes a blocking of the guard from movement and removal of the protective cap enables a movement of the blocking element to a release position when the engagement surface engages the proximal area allowing the member guard to move.

20 Claims, 6 Drawing Sheets

(51) Int. Cl.
*A61M 5/315* (2006.01)
*A61M 5/32* (2006.01)

(52) U.S. Cl.
CPC .... *A61M 5/31571* (2013.01); *A61M 5/31578* (2013.01); *A61M 5/3202* (2013.01); *A61M 5/3204* (2013.01); *A61M 5/3257* (2013.01); *A61M 2005/2073* (2013.01)

(58) Field of Classification Search
CPC .......... A61M 5/31535; A61M 5/31578; A61M 5/3202; A61M 2005/2073
See application file for complete search history.

(56) References Cited

FOREIGN PATENT DOCUMENTS

| | | | |
|---|---|---|---|
| CN | 105636623 | A | 6/2016 |
| EP | 2361648 | A1 | 8/2011 |
| EP | 2745866 | A1 | 6/2014 |
| EP | 2923714 | A1 | 9/2015 |
| JP | 2015-510802 | A | 4/2015 |
| JP | 2015-513439 | A | 5/2015 |
| TW | I517872 | B | 1/2016 |
| TW | M518569 | U | 3/2016 |
| TW | M520909 | U | 5/2016 |
| WO | 2008/113864 | A1 | 9/2008 |
| WO | 2010/136078 | A1 | 12/2010 |
| WO | 2011/040861 | A1 | 4/2011 |
| WO | 2011/145999 | A1 | 11/2011 |
| WO | 2012/045350 | A1 | 4/2012 |
| WO | 2013/135566 | A2 | 9/2013 |
| WO | 2013/139850 | A1 | 9/2013 |
| WO | 2015/113172 | A1 | 8/2015 |
| WO | 2015/169608 | A1 | 11/2015 |
| WO | 2016/015165 | A1 | 2/2016 |
| WO | 2016/051168 | A2 | 4/2016 |

OTHER PUBLICATIONS

Chinese Office Action for CN Application No. 201780032475.0, dated Jul. 22, 2020.

MEDICAMENT DELIVERY DEVICE

CROSS REFERENCE TO RELATED APPLICATIONS

The present application a continuation of U.S. patent application Ser. No. 16/304,865, filed Nov. 27, 2018, which is a U.S. National Phase application pursuant to 35 U.S.C. § 371 of International Application No. PCT/EP2017/060965 filed May 9, 2017, which claims priority to Swedish Patent Application No. 1650778-2 filed Jun. 3, 2016. The entire disclosure contents of these applications are herewith incorporated by reference into the present application.

TECHNICAL AREA

The present disclosure relates to a medicament delivery device comprising safety features ensuring an unaffected device even after e.g. a drop of the device on a hard surface.

BACKGROUND

Many medicament delivery devices on the market today are arranged with a number of features that will facilitate the use of the device and in particular since the devices more and more are intended to be handled by the patients themselves. The added functionality is also an advantage when the medicament delivery devices comprise injection needles since many patients feel uncomfortable seeing the needle and also feel reluctant regarding penetration of the needle. In that respect, an added functionality such as automatic penetration mechanisms as well as automatic injection mechanisms, to mention some features.

Many medicament delivery devices that are arranged with automatic features and functions are often arranged with some sort of actuation member at the proximal end of the device. These actuation members may be sleeve-like members that are pressed against the dose delivery site whereby they can be moved in the distal direction in relation to the device, thereby activating a certain feature or function. In addition, these sleeve-like members may also function as medicament delivery member guards that hide or cover the medicament delivery member before, during and after dose delivery.

Even though this solution may function very well, there is a risk that the device may be accidentally activated if the device is dropped on a hard surface, for example if the user drops the device on the floor. Such an impact may well cause the actuation member at the proximal end of the device to move to such an extent that the device is activated such that a dose of medicament is delivered. This dose is then wasted. If the device is a non-reusable device, then the device has to be discarded without having delivered any medicament to the patient and a new device has to be obtained. Even if the device is re-usable, it has to be reloaded in order to deliver a new dose. Both obtaining a new device or reloading a device is time-consuming and is stress-causing to a patient.

There is thus a demand for devices having an increased functionality regarding minimizing the risk of activation of devices after accidental drops and other types of accidental impacts.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present disclosure is to remedy the drawbacks of the state of the art medicament delivery devices. This aim is obtained by a medicament delivery device according to the features of the independent patent claim. Preferable embodiments of the disclosure form the subject of the dependent patent claims.

The medicament delivery device according to the present disclosure may preferably comprise a generally elongated housing, having a proximal and a distal end. The device is preferably further arranged with a medicament delivery actuation mechanism. The mechanism may be designed in many ways. A preferable solution is to utilize an elongated piston rod that is capable of acting on a stopper of a medicament container.

The piston rod may be arranged to be moved purely manually or by some sort of force. In this respect resilient force members such as springs may be used for creating the necessary force. The force may then be acting directly on the plunger rod or via drive mechanisms such as threaded nuts cooperating with threads on the plunger rod. Further, there may be mechanisms that will activate the force to perform dose delivery. These mechanisms may comprise contact members that will activate the device when the contact member is pressed against a dose delivery site. In this respect the contact member may be a medicament delivery member guard arranged movable in the proximal end of said housing.

The shield will thus surround the delivery member which is an advantage if the person using the device is afraid of medicament delivery members and in particular injection needles. It is also to be understood that the device may further comprise additional functions such as penetration mechanisms for injection needles, which also may be activated by the contact member.

In order to prevent damages to the proximal end of the device and to protect the medicament delivery member before use, a protective cap may be releasibly arranged to said proximal end of said housing. The protective cap may preferably comprise a medicament delivery member shield remover for removing protective members that surround a medicament delivery member before use. It may for example be injection needle sheaths that surround injection needles, keeping them sterile before use, such as rigid needle shields or flexible needle shields.

According to a preferable embodiment of the disclosure, it is characterised by a blocking element that may be arranged to the medicament delivery member guard. The blocking element may be arranged movable between a blocking position and a release position. Further, the blocking element may be arranged with an engagement surface arranged to engage with a proximal area of the housing.

The blocking element is arranged to engage with a surface of the medicament delivery member shield remover, retaining the blocking element in the blocking position, wherein engagement of the engagement surface with the proximal area causes a blocking of the medicament delivery member guard from movement, and wherein removal of the protective cap and the medicament delivery member shield remover enables a movement of said blocking element to a release position when the engagement surface engages the proximal area, allowing the medicament delivery member guard to move.

The advantage with the blocking elements is that they ensure that the medicament delivery member guard is not affected if someone accidentally drops a device onto a surface such as a floor or a table or any other hard surface. The device will thus not by accidence be triggered or components and/or functions will not be moved and/or activated due to accidental wrong handling. The blocking element will thus ensure that the device will stay in operational mode even if the device is not handled in the proper way. The cooperation between the medicament delivery member shield remover of the protective cap provides a robust solution that enables an unlocking of the medicament delivery member guard when the protective cap is removed. Thus the medicament delivery member guard is locked as long as the protective cap with its medicament delivery member shield remover is attached to the medicament delivery device.

According to one favourable solution the blocking element may comprise a member flexible in a generally radial direction of the medicament delivery device from a blocking position to a release position of said medicament delivery member guard when the protective cap is removed. This again ensures that the device is unaffected by any accidental handling until the protective cap is removed. In particular, the medicament delivery member guard is securely locked from any movement by the lock members until the protective cap is removed.

The blocking element may according to one feasible solution comprise comprises a flexible tongue arranged with the contact surface, which in turn is interacting with a stop surface of the device. Preferably the stop surface may comprise a proximal end surface of a housing part of the medicament delivery device. The flexibility of the tongue provides a feature that the material as such entails a desired function, as one such function the blocking elements may comprise clips having resilient properties. The resiliency of the material provides a positive opportunity of obtaining the functions desired and required for the blocking element. Further, a fixed surface of the housing of the device provides a rigid and stable stop surface.

The blocking element may be arranged with an inwardly directed contact surface and wherein the protective cover may be arranged with a generally tubular medicament delivery member shield remover to which the contact surface engages, wherein the medicament delivery member shield remover surrounds and engages a medicament delivery member shield.

Further, the medicament delivery member shield remover may comprise inclined tongues arranged to grip into an outer surface of the medicament delivery member shield. This provides a firm and positive gripping of the medicament delivery member shield by the medicament delivery member shield remover. In order to provide a very secure and firm gripping of the medicament delivery member shield, the medicament delivery member shield remover may be made of metal.

According to yet a favourable aspect of the disclosure, it may further comprise a protective cap holding mechanism, operably arranged to releasibly hold the protective cap.

In line with one favourable solution of the protective cap holding mechanism, the protective cap holding mechanism may comprise a protrusion on a housing part of the device, forming contact surfaces, which contact surfaces are arranged to cooperate with contact surfaces on the protective cap. With this solution, the protective cap is held in place on the housing until a user applies a pulling or twisting force on the protective cap for removal before use.

In that respect, the protective cap may be designed of a material with resilient properties and the contact surfaces may be arranged such that a release force on said protective cap will cause the protective cap to flex and said contact surfaces to be moved out of contact with each other, thereby releasing said protective cap. With the solution, the material properties of the protective cap are utilized for the holding function.

These and other aspects of, and advantages with, the present disclosure will become apparent from the following detailed description of the disclosure and from the accompanying drawings.

BRIEF DESCRIPTION OF DRAWINGS

In the following detailed description of the invention, reference will be made to the accompanying drawings, of which

DETAILED DESCRIPTION

Figure 1:
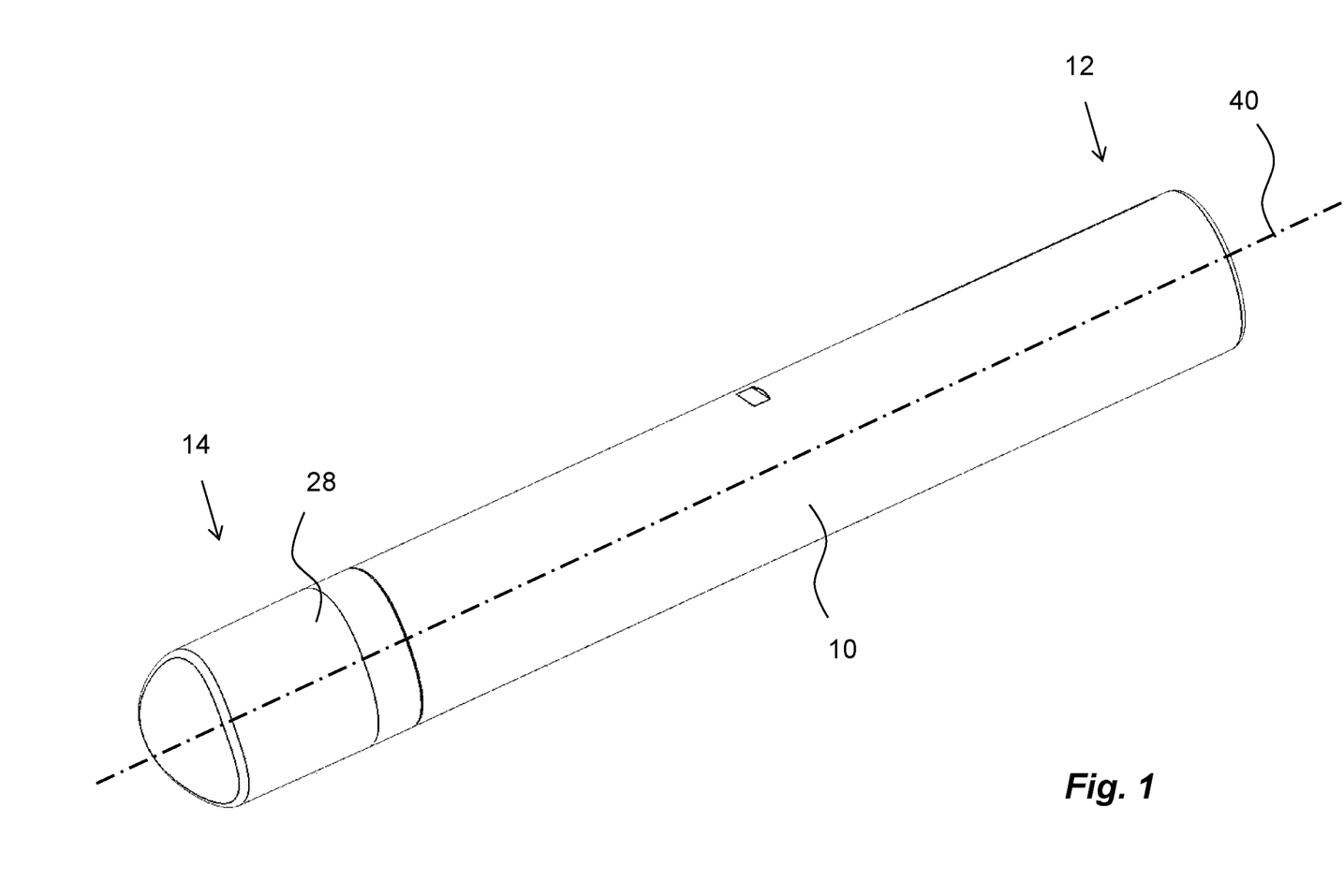
FIG. 1 shows a perspective view of a medicament delivery device comprising the present disclosure.

The embodiment shown in the drawings comprises a generally elongated, tubular housing 10 with a somewhat triangular shape in cross-section, and having a distal end 12 and a proximal end 14, FIG. 1. The housing is arranged to accommodate a medicament delivery actuation mechanism 16, FIG. 2, capable of, upon activation, effecting a delivery of a dose of medicament from a medicament container 18 arranged inside the housing via a medicament delivery member, such as e.g. an injection needle 20, FIG. 3. The injection needle may be protected before use by an appropriate medicament delivery member shield 22, FIG. 2, and in the embodiment shown a so called RNS (rigid needle shield) is utilized. The medicament delivery actuation mechanism may have a number of designs and functions that are not essential to the disclosure and will therefore not be described in detail.

Figure 2:
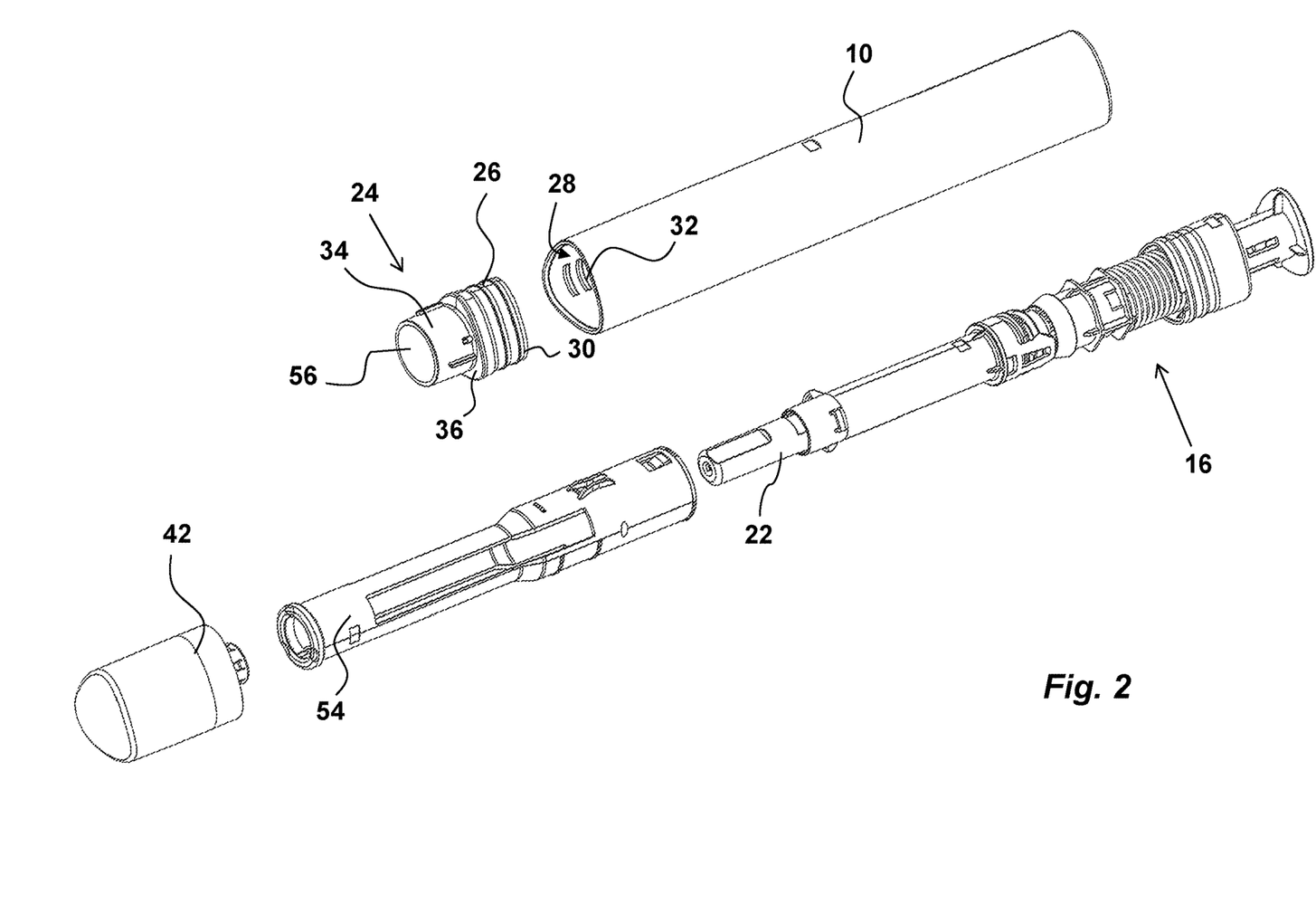
FIG. 2 is an exploded view of the device of FIG. 1.
Figure 3:
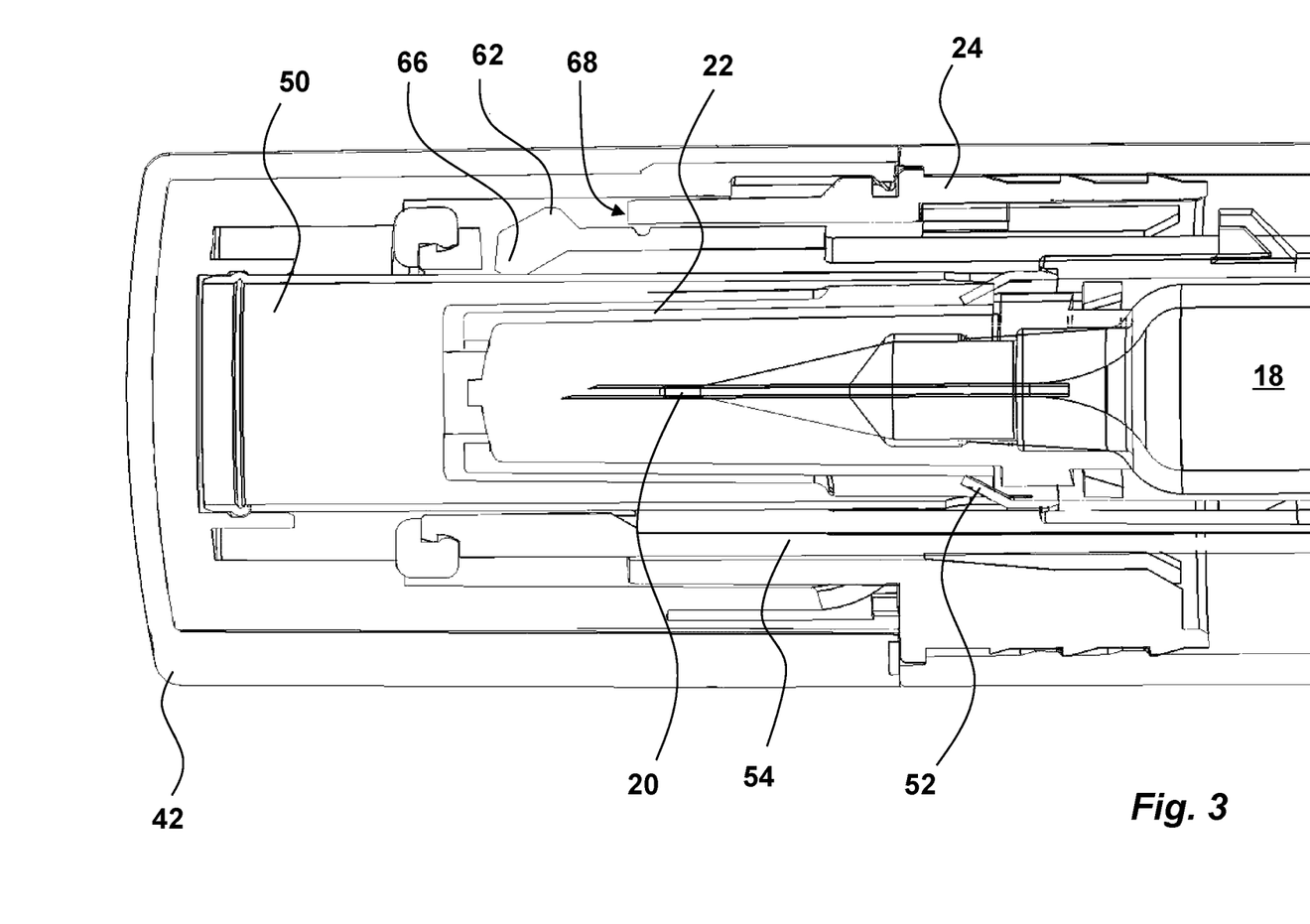
FIG. 3 is a cross-sectional view of a proximal part of the device of FIG. 1, and FIGS. 4-6 each show detailed views of components comprised in the present disclosure.
Figure 4:
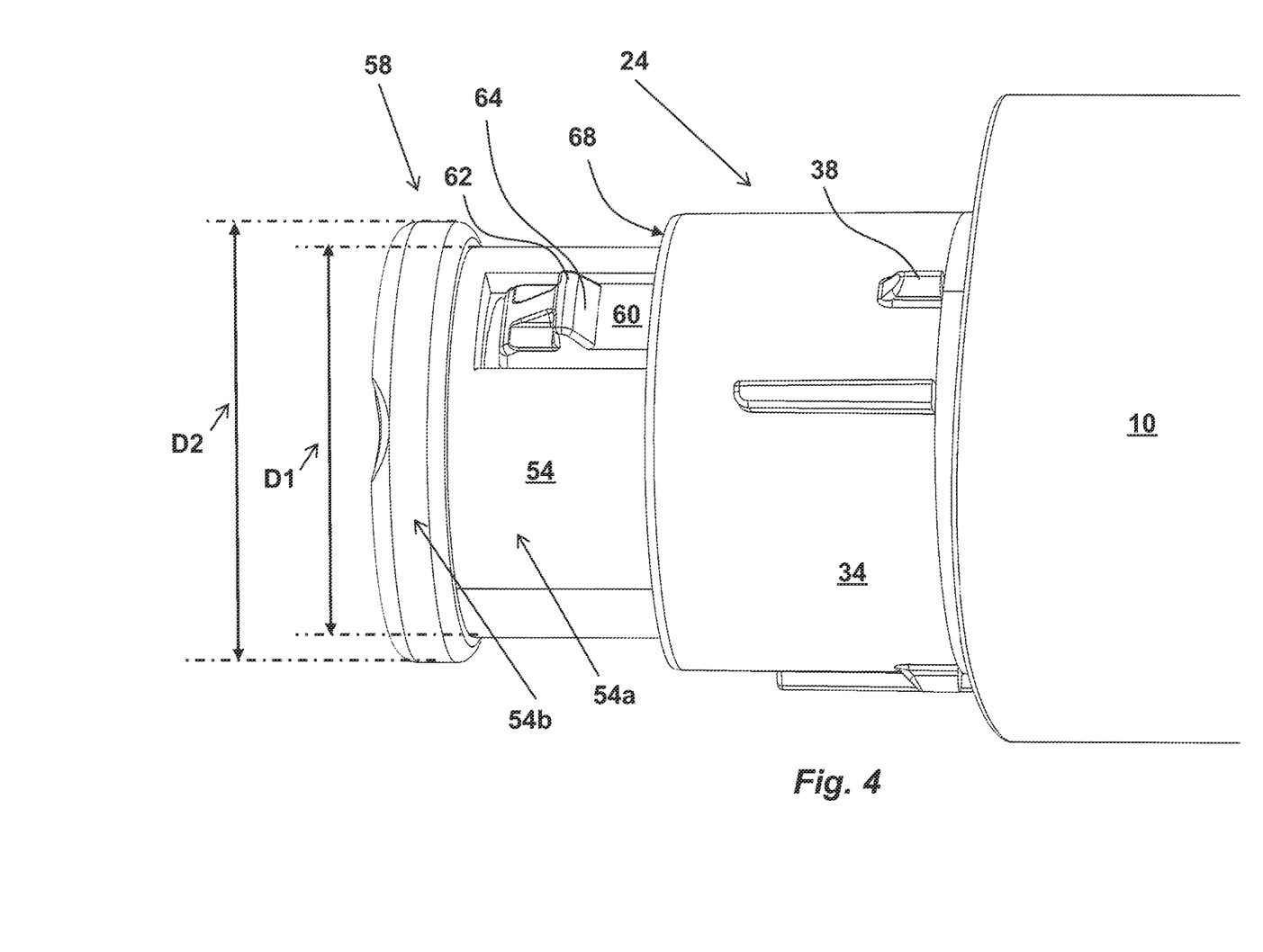

The proximal end of the housing is arranged with an end cover 24, FIGS. 2 and 4, of a generally tubular shape. A distal part 26 of the end cover 24 is arranged with dimensions and a shape generally corresponding to the proximally directed opening 28 of the housing 10. The distal part 26 is arranged with attachment members 30 in the embodiment shown as transversal ledges, which are to engage with transversal ledges 32 on the inner surface of the housing, FIG. 2.

The end cover 24 further comprises a proximal part 34 with a somewhat lesser diameter than the distal part 28. The distal part 26 and the proximal part 34 of the end cover 24 are separated by a generally proximally directed transition surface 36. Further, the end cover 24 is arranged with a first holding member 38 comprised in a protective cap holding mechanism, FIG. 4, on the outer surface of the proximal part 34, that in the embodiment shown is arranged as a ledge or protrusion positioned generally in line with the longitudinal direction 40 of the device. The protrusion 38 may have somewhat inclined side surfaces as seen in FIG. 4.

Figure 5:
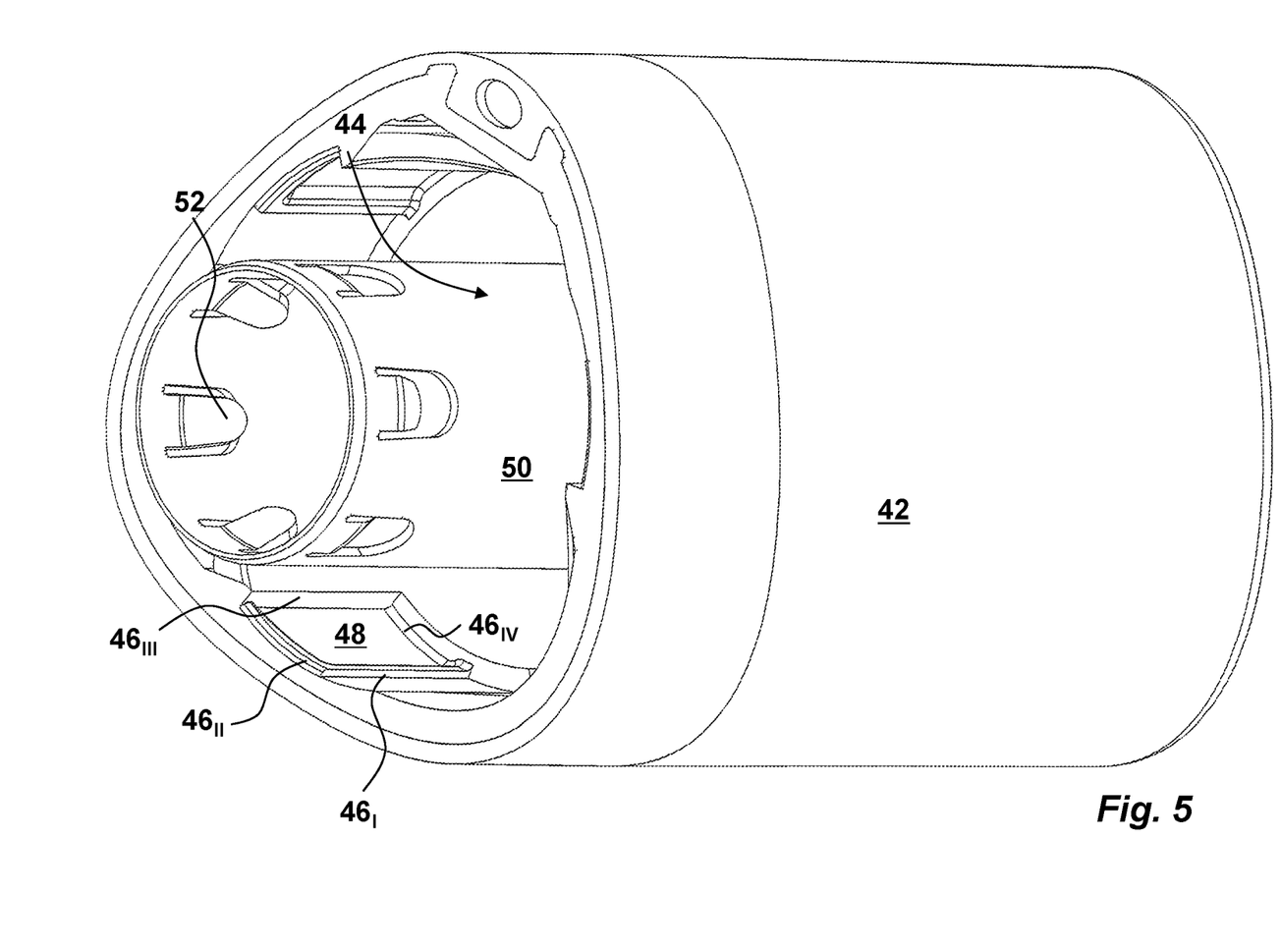

A protective cap 42, FIGS. 2, and 5, is further arranged to the device. The protective cap 42, is generally tubular in shape and with a similar form as the housing 10. It has a distally directed opening 44, which has a diameter somewhat larger than the outer diameter of the proximal part 34 of the end cover 24, such that the protective cap 42 will fit around the proximal part 34. On the inner surface of the protective cap 42 a second holding member 46 is arranged, designed to interact with the first holding member 38, comprised in the protective cap holding mechanism. In the embodiment shown it is arranged as a number of ledges 46 I-IV, forming a space 48 where the first holding member 38 is positioned when the protective cap is attached to the housing and the end cover. Two of the ledges 46 I and II have a lesser height, the function of which will be explained below.

The protective cap 42 is further arranged with a medicament delivery member shield remover, in the embodiment shown in the form of a tubular needle shield remover 50 attached to a distally directed wall surface. The needle shield remover 50 is arranged with inwardly extending inclined tongues 52, which are capable of gripping into the outer surface of the RNS 22, FIG. 3.

The device further comprises a medicament delivery member guard 54, FIGS. 2 and 4, in the form of a generally elongated tubular member having an outer surface 54a and a proximal end comprising a radially extending flange 54b, where the outer surface 54a of the proximal part has a diameter D1 only somewhat smaller than the inner diameter of an opening 56 at the proximal end of the end cover 24. Flange 54b can have an outer diameter D2 that is greater than the outer diameter D1 of the outer surface 54a. The medicament delivery member guard 54 is arranged slidable in the longitudinal direction of the device from positions where the medicament delivery member 20 is covered to positions where the medicament delivery member is exposed during delivery of medicament. An actuator (not shown) may be arranged to force the medicament delivery member guard 54 in the proximal direction.

Figure 6:
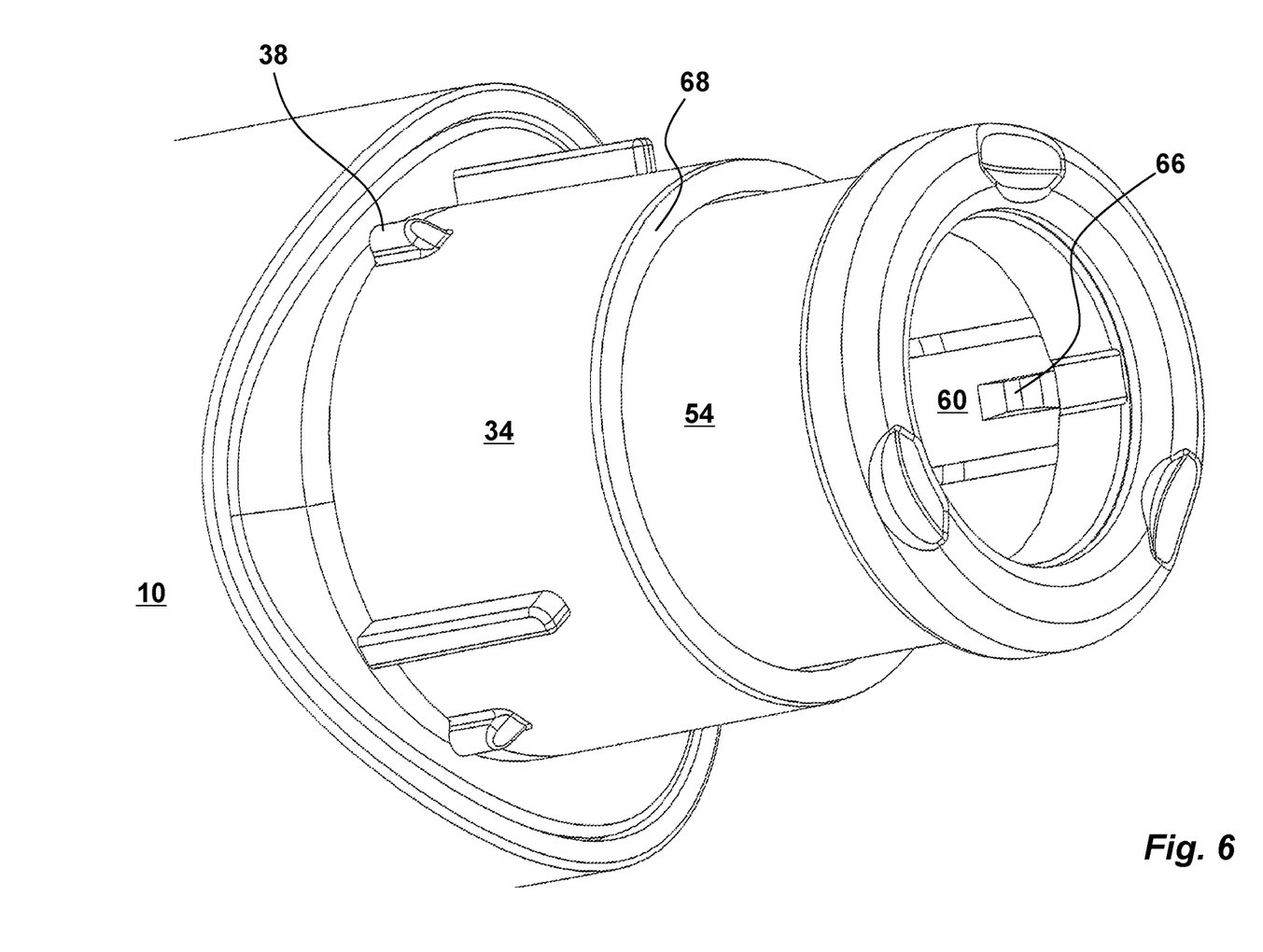

The outer surface of the medicament delivery member guard 54 is arranged with a blocking element 58, FIG. 4. In the embodiment shown it is arranged as a tongue 60 by a U-shaped cut-out in the medicament delivery member guard 54, having a free end of the tongue 60 facing the proximal direction. An outwardly facing surface of the tongue 60 is arranged with a protrusion 62. The protrusion 62 is arranged with a distally directed surface 64 having a certain inclination in relation to the longitudinal direction 40 of the device. The free end of the tongue is further arranged with an inwardly directed protrusion 66, FIGS. 3 and 6, the function of which will be explained below.

When the device is in an initial state with the medicament delivery member guard 54 in an initial position in relation to the housing 10 and the protective cap 42 is attached to the device, the first and second holding members 38, 46 interact to releasibly hold the protective cap 42 to the housing 10 such that the protrusion 38 of the first holding member is within the area 48 of the ledges 46 of the second holding member. Further, the needle shield remover 50 is surrounding the needle shield 22 and the inwardly directed protrusion 66 of the tongue 60 is in contact with the outer surface of the needle shield remover 50, FIG. 3. Thus the tongue 60 of the blocking element 58 is prevented from moving inwardly radially. Further, the outwardly directed protrusion 62 of the tongue 60 is arranged to block any movement in the distal direction of the medicament delivery member guard 54 in that the protrusion 62 will engage a contact surface in the form of a proximally directed surface 68 of the end cover 24. Thus, the medicament delivery device guard 54 is prevented from moving if the device should accidentally be dropped on a hard surface such as a floor, thereby preventing unintended activation of the device.

When the device is to be used, the protective cap 42 may be turned whereby the protrusion 38 of the first holding member will pass over the lower ledge $46_I$, after which the protective cap is free to be removed. As an alternative, the protective cap 42 may be pulled in the proximal direction whereby the protrusion 38 will pass over the lower ledge $46_{II}$. Due to the connection of the needle shield remover 50 with the RNS 22, the RNS 22 will be removed when the protective cap 42 is removed, thus rendering the medicament delivery member 20 ready for use, FIG. 6. When the protective cap 42 is removed, the proximal end of the device, which preferably is the proximal end of the medicament delivery member guard 54, can be pressed against a dose delivery site.

The pressing of the medicament delivery guard 54 will cause it to move in the distal direction in relation to the housing and the end cover 24. Due to that the tongue now is free to move in the radial direction because the inwardly directed protrusion 66 is no longer in contact with the needle shield remover 50, FIG. 6, the outwardly directed protrusion 62 of the tongue 60 can pass the proximally directed surface 68 of the end cover. The passing is facilitated by the inclined surface 64 of the outwardly directed protrusion. Thus, the distal movement of the medicament delivery member guard 54 in the distal direction will cause an activation of the device for delivering a dose of medicament.

It is to be understood that the embodiment described above and shown in the drawings is to be regarded only as a non-limiting example of the disclosure and that it may be modified in many ways within the scope of the patent claims.

The invention claimed is:

1. An activation mechanism for a medicament delivery device comprising:
    a housing having a proximal end terminating in a proximally directed surface; and
    a guard axially moveable relative to the housing and comprising:
    a blocking element having a blocking position and a release position; and
    a radial extending flange configured to engage a dose delivery site,
    wherein when the guard is in an initial position, the blocking element is not in contact with the proximally directed surface of the housing,
    wherein when the flange is pressed against the dose delivery site, the blocking element, when in the release position, will move distally and axially past the proximally directed surface of the housing, and
    wherein when the blocking element is in the blocking position, the guard is free to move distally and axially relative to the housing until the blocking element engages the proximally directed surface of the housing such that the engagement of the blocking element with the proximally directed surface of the housing will prevent further axial movement of the guard in the distal direction.

2. The activation mechanism of claim 1, wherein the blocking element comprises a flexible tongue that projects radially outward from an outer surface of the guard.

3. The activation mechanism of claim 1, wherein the blocking element is fixed radially when the blocking element is in the blocking position.

4. The activation mechanism of claim 1, wherein the flange has a larger diameter than an outer surface of the guard.

5. The activation mechanism of claim 1 where the blocking element is located on an outside surface of the guard and comprises a flexible tongue having an inwardly directed contact surface that is engaged with a needle shield remover when the flexible tongue is fixed radially.

6. The activation mechanism of claim 5 where the flexible tongue comprises an engagement surface projecting radially outward that prevents distal axial movement of the guard when the blocking element is in the blocking position and the guard has moved distally from the initial position relative to the proximally directed surface of the housing.

7. The activation mechanism of claim 5 where the flexible tongue is flexed radially inward when the guard moves distally and axially past the proximally directed surface of the housing as the guard is pressed against the dose delivery site.

8. The activation mechanism of claim 5 where the flexible tongue further comprises an outwardly directed protrusion having an inclined surface.

9. The activation mechanism of claim 1, wherein blocking element comprises a flexible tongue having a radially outward directed protrusion having a distally directed surface.

10. The activation mechanism of claim 9, wherein the protrusion is not engaged with the proximally directed surface of the housing when the guard is in the initial position.

11. The activation mechanism of claim 10, wherein the protrusion is not engaged with the proximally directed surface of the housing when the guard is pressed against the dose delivery site and the blocking element is in the release position.

12. The activation mechanism of claim 9, wherein the protrusion will engage with and will directly abut the proximally directed surface of the housing when the guard is moved axially and distally when the blocking element is in the blocking position.

13. The activation mechanism of claim 9, wherein the distally directed surface moves axially in a distal direction when the flange is pressed against the dose delivery site such that the distally directed surface contacts the proximally directed surface of the housing causing the protrusion to move radially inward and move past the proximally directed surface of the housing.

14. An activation mechanism for a medicament delivery device comprising:
a housing having a proximal end terminating in a proximally directed surface;
a protective cap releasably connected to the proximal end of the housing;
a shield remover axially fixed to the protective cap; and
a guard axially moveable relative to the housing and comprising:
a blocking element having a blocking position and a release position; and
a radial extending flange configured to engage a dose delivery site,
wherein when the guard is in an initial position, the blocking element is not in contact with the proximally directed surface of the housing,
wherein when the flange is pressed against the dose delivery site, the blocking element, when in the release position, will move distally and axially past the proximally directed surface of the housing, and
wherein when the blocking element is in the blocking position, the guard is free to move distally and axially relative to the housing until the blocking element engages the proximally directed surface of the housing such that the engagement of the blocking element with the proximally directed surface of the housing will prevent further axial movement of the guard in the distal direction.

15. The activation mechanism of claim 14, wherein the blocking element is engaged with a surface of the shield remover to retain the blocking element in the blocking position.

16. The activation mechanism of claim 15, wherein removal of the protective cap from the housing disengages the shield remover from the blocking element such that the blocking element transitions from the blocking position to the release position.

17. The activation mechanism of claim 14, wherein the blocking element comprises a flexible tongue having a free end comprising an inwardly directed protrusion that engages an outer surface of the shield remover.

18. The delivery device of claim 17, wherein the flexible tongue flexes radially inward during distal movement of the guard moving from an unlocked state to an activation state.

19. The activation mechanism of claim 14, wherein the shield remover comprises inclined tongues arranged to grip onto an outer surface of a medicament delivery member shield.

20. The activation mechanism of claim 14, wherein the protective cap comprises a first holding member in the form of a protrusion and the housing comprises a second holding member that engages the first holding member when the protective cap is releasably connected to the housing, wherein the protective cap is constructed with a material having resilient properties such that exerting a release force on the protective cap will cause the protective cap to flex disengaging the first and second holding members, thereby releasing the protective cap from the housing.

* * * * *